United States Patent
Luo et al.

(10) Patent No.: US 9,615,814 B2
(45) Date of Patent: *Apr. 11, 2017

(54) ULTRASONIC BONE ASSESSMENT APPARATUS AND METHOD

(75) Inventors: Gangming Luo, Elmhurst, NY (US); Jonathan J. Kaufman, Brooklyn, NY (US)

(73) Assignee: CyberLogic, Inc., New York City, NY (US)

( * ) Notice: Subject to any disclaimer, the term of this patent is extended or adjusted under 35 U.S.C. 154(b) by 473 days.

This patent is subject to a terminal disclaimer.

(21) Appl. No.: 13/015,141

(22) Filed: Jan. 27, 2011

(65) Prior Publication Data
US 2011/0125015 A1 May 26, 2011

Related U.S. Application Data

(63) Continuation-in-part of application No. 11/954,554, filed on Dec. 12, 2007, now Pat. No. 7,901,356.

(60) Provisional application No. 60/874,654, filed on Dec. 13, 2006, provisional application No. 60/875,088, filed on Dec. 15, 2006.

(51) Int. Cl.
*A61B 8/08* (2006.01)

(52) U.S. Cl.
CPC .................... *A61B 8/0875* (2013.01)

(58) Field of Classification Search
None
See application file for complete search history.

(56) References Cited

U.S. PATENT DOCUMENTS

| | | |
|---|---|---|
| 3,847,141 A | 11/1974 | Hoop |
| 4,361,154 A | 11/1982 | Pratt, Jr. |
| 4,421,119 A | 12/1983 | Pratt, Jr. |
| 4,774,959 A | 10/1988 | Palmer et al. |
| 4,913,157 A | 4/1990 | Pratt, Jr. et al. |

(Continued)

FOREIGN PATENT DOCUMENTS

WO    WO 2004/017813    *  8/2013

OTHER PUBLICATIONS

Barkman, R. et al., "Assessment of the Geometry of Human Finger Phalanges Using Quantitative Ultrasound in Vivo," 11 Osteoporosis Intl. pp. 745-755 (2000).

(Continued)

*Primary Examiner* — Christopher Cook
(74) *Attorney, Agent, or Firm* — Reising Ethington P.C.

(57) ABSTRACT

An invention is disclosed for locating a region of interest in the calcaneus. A pair of ultrasound transducers are positioned on the medial and lateral sides of the heel, respectively. The positioning is based on a size of a portion of the body of a subject upon whom the ultrasound assessment of the calcaneus is to be made. In a presently preferred embodiment, the length of the foot from the back to the head of the first metatarsal is used in conjunction with a proportionality constant and an angle, to position the pair of transducers. The positioning so obtained facilitates (i) reproducible measurements and (ii) comparisons of the results obtained in one person with another, because relatively analogous portions of the highly heterogeneous calcanei are assessed in both. In an alternative embodiment, a single transducer is positioned similarly on the heel, operating in pulse-echo mode.

22 Claims, 5 Drawing Sheets

(56) References Cited

U.S. PATENT DOCUMENTS

| | | | |
|---|---|---|---|
| 4,926,870 A | | 5/1990 | Brandenburger |
| 4,941,474 A | | 7/1990 | Pratt, Jr. |
| 4,976,267 A | | 12/1990 | Jeffcott et al. |
| 5,054,490 A | | 10/1991 | Rossman et al. |
| 5,119,820 A | | 6/1992 | Rossman et al. |
| 5,235,981 A | | 8/1993 | Hascoet et al. |
| 5,259,384 A | | 11/1993 | Kaufman et al. |
| 5,309,898 A | | 5/1994 | Kaufman et al. |
| 5,343,863 A | | 9/1994 | Weiner et al. |
| 5,452,722 A | * | 9/1995 | Langton .................. 600/442 |
| 5,458,130 A | | 10/1995 | Kaufman et al. |
| 5,520,612 A | | 5/1996 | Winder et al. |
| 5,524,624 A | | 6/1996 | Tepper et al. |
| 5,547,459 A | | 8/1996 | Kaufman et al. |
| 5,564,423 A | | 10/1996 | Mele et al. |
| 5,651,363 A | | 7/1997 | Kaufman et al. |
| 5,713,361 A | * | 2/1998 | Ohtomo .................. 600/438 |
| 5,749,363 A | | 5/1998 | Ishii et al. |
| 5,752,924 A | | 5/1998 | Kaufman et al. |
| 5,785,656 A | | 7/1998 | Chiabrera et al. |
| 5,822,223 A | * | 10/1998 | Genest .................. 702/155 |
| 5,879,301 A | | 3/1999 | Chiabrera et al. |
| 5,921,929 A | | 7/1999 | Goll et al. |
| 6,015,383 A | * | 1/2000 | Buhler et al. .................. 600/437 |
| 6,090,046 A | | 7/2000 | Goll et al. |
| 6,163,971 A | * | 12/2000 | Humphries et al. ............ 33/515 |
| 6,200,266 B1 | | 3/2001 | Shokrollahi et al. |
| 6,221,019 B1 | | 4/2001 | Kantorovich |
| 6,231,528 B1 | | 5/2001 | Kaufman et al. |
| 6,234,969 B1 | | 5/2001 | Chaintreuil et al. |
| 6,251,088 B1 | | 6/2001 | Kaufman et al. |
| 6,277,076 B1 | | 8/2001 | Morris et al. |
| 6,328,695 B1 | | 12/2001 | Wammen et al. |
| 6,352,512 B1 | | 3/2002 | Wilson et al. |
| 6,364,837 B1 | | 4/2002 | Mazess et al. |
| 6,371,916 B1 | | 4/2002 | Buhler et al. |
| 6,436,042 B1 | | 8/2002 | Cadossi et al. |
| 6,468,215 B1 | | 10/2002 | Sarvazyan et al. |
| 6,491,635 B1 | | 12/2002 | Mazess et al. |
| 6,517,487 B1 | | 2/2003 | Mazess et al. |
| 6,520,914 B2 | | 2/2003 | Morris et al. |
| 6,585,649 B1 | | 7/2003 | Mendlein et al. |
| 6,641,537 B2 | | 11/2003 | Morris et al. |
| 6,652,473 B2 | | 11/2003 | Kaufman et al. |
| 6,740,041 B2 | | 5/2004 | Faulkner et al. |
| 6,835,178 B1 | | 12/2004 | Wilson et al. |
| 6,899,680 B2 | | 5/2005 | Hoff et al. |
| 7,901,356 B2 | * | 3/2011 | Luo et al. .................. 600/438 |

OTHER PUBLICATIONS

Cheng S. et al., "Influence of Region of Interest and Bone Size in Calcaneal BMD: Implications for the Accuracy of Quantitative Ultrasound Assessments at the Calcaneus," 75 The British Journal of Radiology (Jan. 2002) pp. 59-68.

Damilakis, J. et al., "Imaging Ultrasonometry of the Calcaneus: Dependence on the Calcaneal Area," 67 Calcified Tissue International (2000) pp. 24-28.

De Terlizzi, Francesca et al., "Influence of Bone Tissue Density and Elasticity on the Ultrasound Propagation: An in Vitro Study," 15 Journal of Bone and Mineral Research No. 12 pp. 2458-2466 (2000).

Gluer, Claus C., "Quantitative Ultrasound Techniques for the Assessment of Osteoporosis: Expert Agreement on Current Status," 12 Journal of Bone and Mineral Research No. 8 pp. 1280-1288 (1997).

Haiat, G. et al., "In Vitro Speed of Sound Measurement at Intact Human Femur Specimens," 31 Ultrasound in Medicine and Biology No. 7 pp. 987-996 (2005).

Higuit, Ricardo Tokio et al., "Ultrasonic Densitometer Using a Multiple Reflection Technique," 49 IEEE Transactions on Ultrasonics, Ferroelectrics and Frequency Control No. 9, pp. 1260-1268 (Sep. 2002).

Kaufman, Jonathan J. et al., "Perspectives Ultrasound Assessment of Bone," 8 Journal of Bone and Mineral Research No. 5 pp. 517-525 (1993).

Langton, C.M. et al., "Comparison of Bone Mineral Density and Quantitative Ultrasound of the Calcaneus: Site-Matched Correlation and Discrimination of Axial BMD Status," The British Journal of Radiology (Jan. 2000) pp. 31-35.

Wear, Keith A., "Autocorrelation and Cepstral Methods for Measurement of Tibial Cortical Thickness," 50 IEEE Transactions on Ultrasonics, Ferroelectrics and Frequency Control No. 6, pp. 655-660 (Jun. 2003).

Wuster, C. et al., "Phalangeal Osteosonogrammetry Study: Age-Related Changes, Diagnostic Sensitivity, and Discrimination Power," 15 Journal of Bone and Mineral Research No. 8, pp. 1603-1614 (2000).

Ye, Shigong et al., "Ultrasound Shear Wave Imaging for Bone," 26 Ultrasound in Medicine and Biology No. 5, pp. 833-837.

Office Action issued in priority U.S. Appl. No. 11/954,554 (Feb. 16, 2010).

Reply to Office Action filed in priority U.S. Appl. No. 11/954,554 (Jul. 16, 2010).

Office Action issued in priority U.S. Appl. No. 11/954,554 (Sep. 29, 2010).

Reply to Office Action filed in priority U.S. Appl. No. 11/954,554 (Oct. 7, 2010).

Notice of Allowability and Examiner Interview Summary issued in priority U.S. Appl. No. 11/954,554 (Oct. 28, 2010).

Applicant Interview Summary filed in priority U.S. Appl. No. 11/954,554 (Nov. 15, 2010).

* cited by examiner d = αL
= 0.23 x 18 cm
= 4.14 cm

θ = 50°
x: Center of ROI

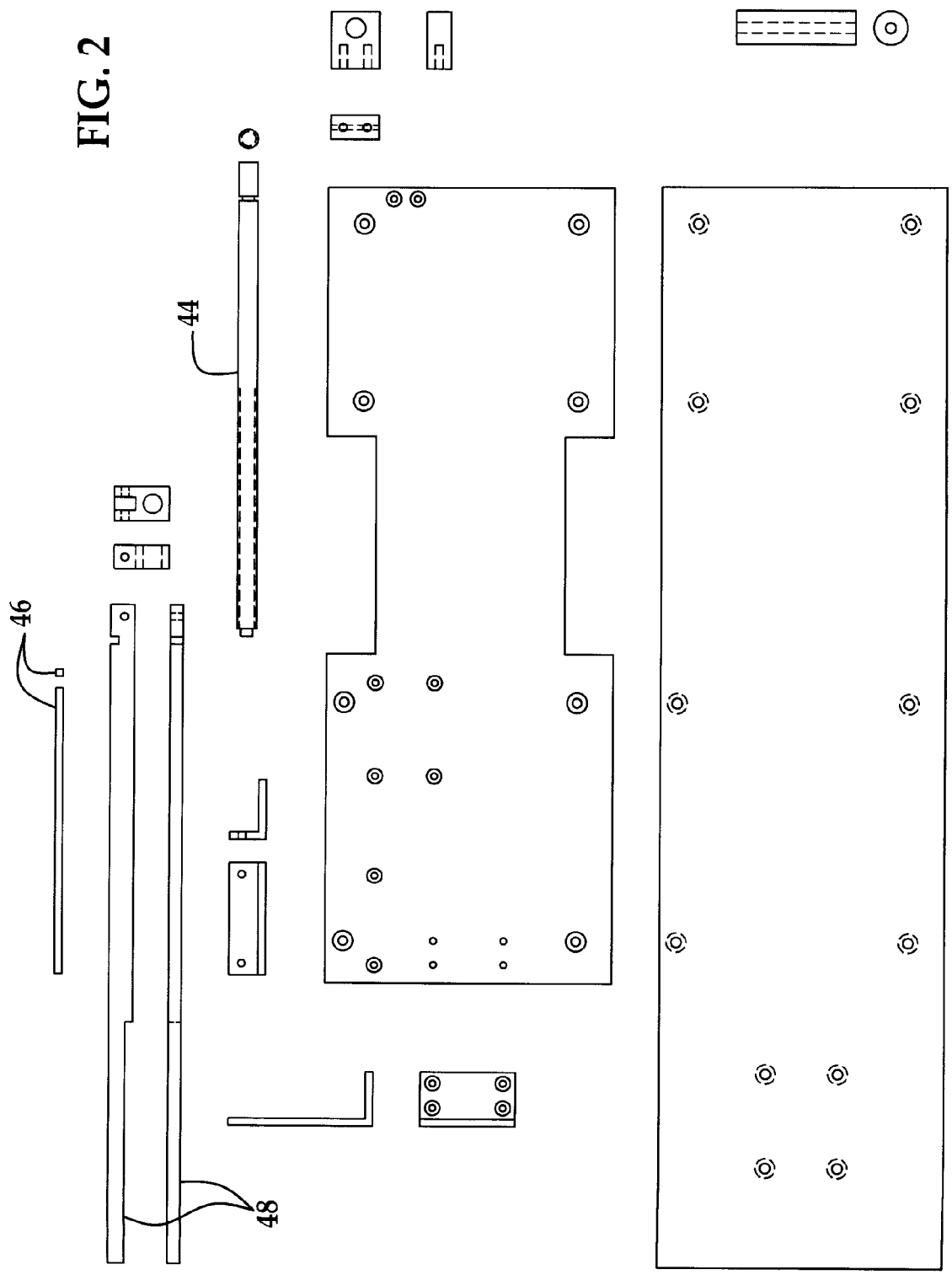

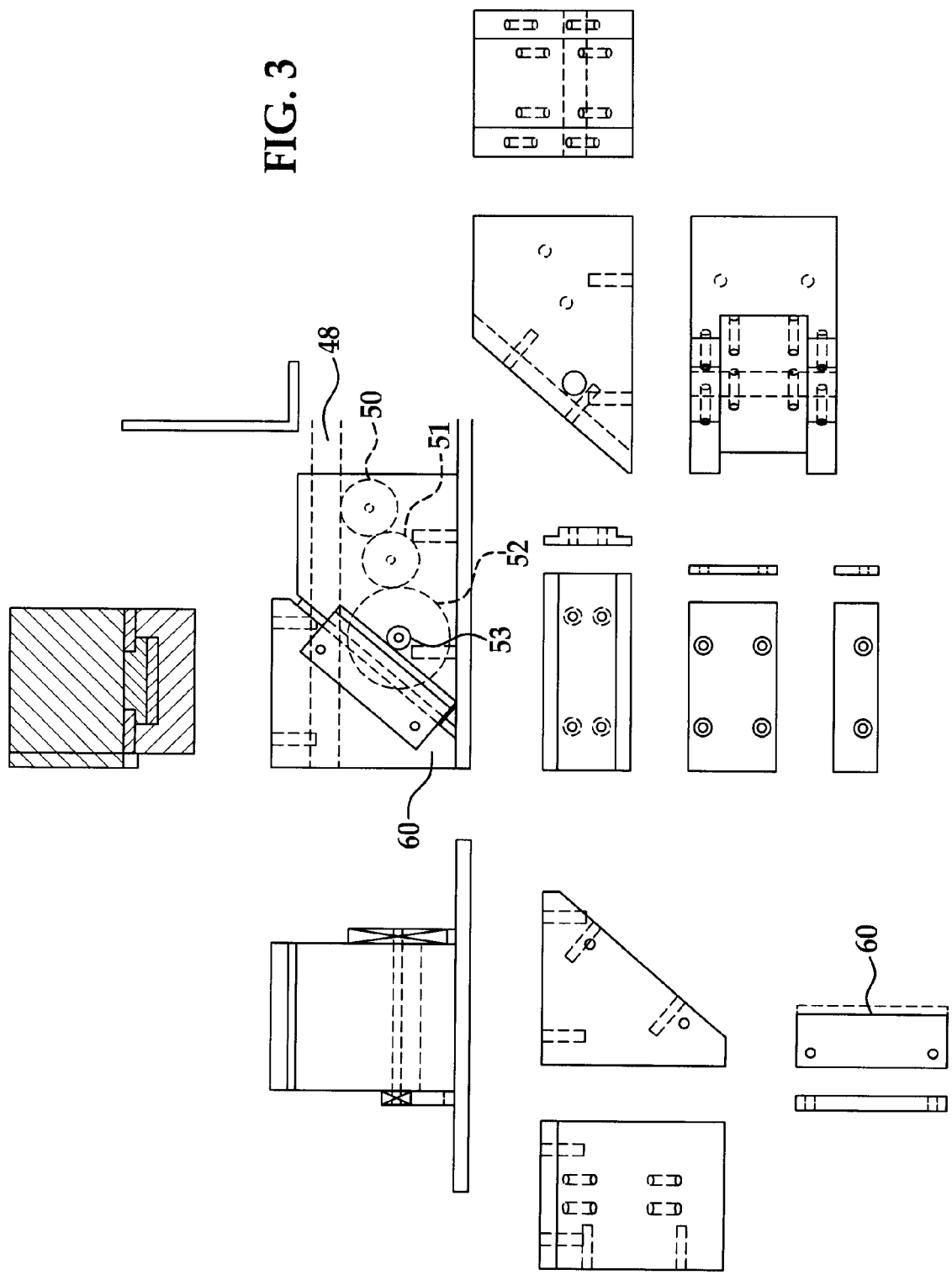

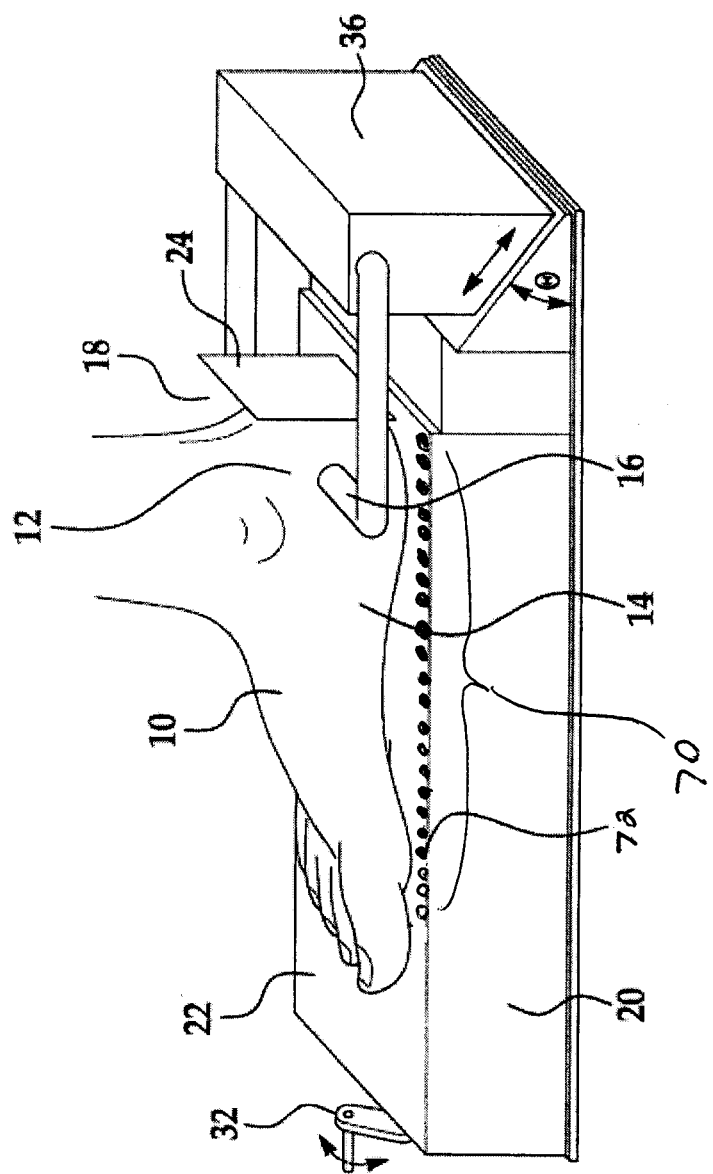

ULTRASONIC BONE ASSESSMENT APPARATUS AND METHOD

RELATED U.S. APPLICATIONS

This application is a continuation-in-part of U.S. patent application Ser. No. 11/954,554 filed Dec. 12, 2007, the entire disclosure of which is incorporated herein by reference, which claims priority to U.S. Provisional Patent Application Ser. No. 60/874,654, filed Dec. 13, 2006, the entire disclosure of which is incorporated herein by reference and claims priority to U.S. Provisional Patent Application Ser. No. 60/875,088, filed Dec. 15, 2006, the entire disclosure of which is incorporated herein by reference.

FIELD OF THE INVENTION

The present invention relates generally to apparatus and method for non-invasively and quantitatively evaluating bone tissue in vivo. More specifically, the invention pertains to osteoporosis diagnosis, bone fracture risk assessment, and bone fracture diagnosis using an ultrasound apparatus and method. Even more specifically, the invention relates to a method and apparatus for locating a region of interest within a calcaneus that allows for both reproducible and comparative measurements of a set of ultrasound parameters associated with a given subject or set of subjects.

BACKGROUND OF THE INVENTION

In recent years, ultrasound has received a great deal of attention as a new technique for noninvasive assessment of bone, and numerous attempts have been made to use ultrasound energy for evaluating the condition of bone tissue in vivo, and thus for determining a measure of osteoporosis and assessing bone fracture risk.

In particular, Hoop discloses in U.S. Pat. No. 3,847,141 a device to measure bone density as a means for monitoring calcium content of the involved bone. A pair of opposed ultrasonic transducers is applied to opposite sides of a subject's finger, such that recurrent pulses transmitted via one transducer are 'focused' on the bone, while the receiver response of the other transducer is similarly "focused" to receive pulses that have been transmitted through the bone. The circuitry in Hoop is arranged such that filtered reception of one pulse triggers the next pulse transmission; the filtering is by way of a bandpass filter, passing components of received signals in the 25 kHz to 125 kHz range only; and the observed frequency of retriggering is believed to be proportional to the calcium content of the bone. Thus Hoop is concerned only with what he defines to be transit time for pulses in the indicated band.

Pratt, Jr. deals with establishing, in vivo, the strength of bone in a live being such as a horse. In U.S. Pat. No. 4,361,154, the inventor solves the problem posed by measuring transit time from "launch" to "reception" of pulses of 0.5 MHz and 1.0 MHz through the bone and soft tissue, and from measurement of pulse-echo time, to thereby derive a measurement of transit time through bone alone. A data bank enables the evaluation of the bone condition from the measured transit times. U.S. Pat. No. 4,913,157, also granted to Pratt, Jr., operates on the same general principle of transit time/velocity deduction, using the latter preferred frequency of 2.25 MHz as the base frequency of pulsed "launchings" and a technique of matched filtering/Fourier transform filtering for further analyzing received pulses.

Palmer et al. disclose in U.S. Pat. No. 4,774,959 a bone measurement system deriving the slope of the relation between ultrasonic frequency and attenuation of a sequence of tone signals. Being in the range of 200 kHz to 600 kHz, the signals are applied to one transducer and received by another transducer. The passage of the signals between the two transducers with and without the intervening presence of a heel bone is compared, with the assumption that the frequency/attenuation relation is a straight line, i.e., of constant slope.

U.S. Pat. No. 4,926,870 granted to Brandenburger discloses another in vivo bone analysis system which depends upon measuring transit time for an ultrasonic signal along a desired path through bone. A "canonical" waveform, determined by previous experience to be on the correct path, is used for comparison against received signals for transmission through the patient's bone, while the latter is reoriented until the received signal indicates that the bone is aligned with the desired path. Again, ultrasonic velocity through the patient's bone is assumed to have been determined from measured transit time.

Rossman et al. disclose in U.S. Pat. No. 5,054,490 an ultrasound densitometer for measuring physical properties and integrity of bone, upon determination of a transit time through bone. Alternatively, the Rossman et al. device compares absolute attenuation of specific frequency components of ultrasound signals through the bone with the absolute attenuation of the same frequency components through a medium of known acoustic properties.

Mele et al., disclose in U.S. Pat. No. 5,564,423, and in a subsequent related Patent by Cadossi et al. (U.S. Pat. No. 6,436,042), disclose a device that measures the "amplitude dependent speed of sound" through a bony member in a living body. The method relies on the visual display of the received ultrasound signal, and the selection of a specific portion of the waveform for analysis.

Significant steps in advancing ultrasound bone assessment have been made by Kaufman et al. (in U.S. Pat. Nos. 5,259,384 and 5,651,363) and by Chiabrera et al. (in U.S. Pat. Nos. 5,785,656 and 5,879,301). In these Patents, an estimate of a "bone transfer function" associated with a given bone is obtained in a statistically optimal fashion, and parametric estimates of the phase and attenuation functions associated with it are determined. The disclosed methods also describe the use of 2D array transducers for obtaining more reproducible estimates of the bone density, architecture, and fracture risk.

Notwithstanding the advances made in the past in previous attempts, as exemplified by the above-mentioned apparatuses and methods, there are still additional improvements needed in order to make ultrasound assessment a widely used technique for accurately and precisely assessing the bone density, architecture, quality, fracture diagnosis, and fracture risk of a subject.

SUMMARY OF THE INVENTION

It is accordingly a primary object of this invention to provide an improved method and apparatus for characterizing and determining non-invasively the properties of bone. A more particular though not limiting object of the invention is to provide a method and apparatus for non-invasive and quantitative evaluation of bone tissue in vivo, to make accurate and precise osteoporosis diagnosis and monitoring possible.

Another object is to meet the above objects in such a way that the bone tissue evaluation and the osteoporosis diagnosis may be performed in a much more convenient and reliable manner than those previously used.

A further object is to meet the above object in such a way that the bone tissue evaluation and the osteoporosis diagnosis may be performed with relatively more simple and inexpensive means than those previously used.

A still further object is to locate a region of interest of the calcaneus that is clinically relevant to assessment of osteoporosis, adjusts to the size of the calcaneus thereby maintaining the same relative region of interest across subjects, and at the same time maintains excellent reproducibility.

As compared with the prior art, the invention utilizes a novel method for reliably and reproducibly locating a region of interest (ROI) in a given subject in order to assist in achieving the indicated objectives. In particular, in the present invention a pair of ultrasound transducers are moved at a given angle and distance, the distance which is selected based on a measurement of a size of a portion of said subject's body.

Accordingly, the present invention utilizes a new configuration to identify a ROI of a calcaneus of a living being, to more conveniently, accurately and precisely determine the characteristics of the calcaneus—to thereby determine one or more of the bone properties such as fracture risk, strength, density, quality, and/or architecture of the bone. The advantage of such an approach is its inherent simplicity and convenience, as well as its increased sensitivity to the underlying state of the interrogated bone. This is in contrast to the prior art which can not extract as much information on the underlying bone in such a convenient and effective manner.

The invention in its presently preferred form of a method and apparatus of locating and identifying a region of interest of a calcaneus, achieves the foregoing objectives by reproducibly placing one or more ultrasound transducers according to a size associated with a given subject. Prior methods have typically used a fixed ROI. For example, in this type of ROI-determination, ultrasound transducers are fixed relative to the fixture into which a subject's foot was placed. This can lead to a reasonable degree of reproducibility per se, but it suffers from the fact that a different portion of the calcaneus will generally be measured in different people. This is a consequence of the high degree of heterogeneity of the calcaneus (i.e., different regions within the calcaneus generally have very different bone densities, cortical thicknesses, and trabecular architectures) and also because of the variations in the size of the calcaneus among individuals. Thus, for a fixed placement of transducers, based for example, on a fixed distance from the back of the foot, this will generally lead to highly distinct relative portions of the calcanei associated with different individuals being measured, making meaningful comparisons among subjects quite difficult. An alternative has been described which relies on 2D arrays. Although a plausible technique for addressing the "fixed region of interest" problem, such systems are extremely complex and expensive.

In an attempt to develop a simple non-array apparatus and method for ultrasonically assessing a calcaneus, that offers both good reproducibility and measures relatively the same region of interest among a set of individuals, the present inventors have recognized several key points. The first, and this is the key observation, is that calcaneal size is closely related to the overall size of the foot. The other key observations are that the main location of interest is in the posterior portion of the calcaneus (as determined from data obtained by x-ray absorptiometers), and that this region of interest may generally be found on average at a fixed angle from the horizontal (as determined from comparisons of the images produced by x-ray absorptiometers like the General Electric Lunar PIXI heel DXA machine with plain foot radiographs of many subjects).

In accordance with another embodiment of the invention, a method for positioning one or more ultrasound transducers at a region of interest in a calcaneus in a first foot of a subject is provided. The method includes the step of placing the first foot in a fixture such that a first ultrasound transducer is disposed on one of a medial side and a lateral side of a heel of the first foot. The method further includes the steps of identifying a size associated with one foot of the first foot and a second foot of the subject and locating a marker at a position relative to the first foot, the position of the marker corresponding to the size. The method further includes the step of moving a first ultrasound transducer over a distance from an original position to a new position relative to the first foot wherein the position of the marker and the new position of the first ultrasound transducer are related by a proportionality constant.

In accordance with another embodiment of the invention, an apparatus for positioning one or more ultrasound transducers at a region of interest in a calcaneus in a first foot of a subject is provided. The apparatus includes a fixture configured to receive the first foot and including a first ultrasound transducer configured to be disposed on one of a medial side and a lateral side of a heel of the first foot. The apparatus also includes a marker indicative of a position associated with the first foot, the position corresponding to a size associated with one foot of the first foot and a second foot of the subject. The apparatus further includes means for moving the first ultrasound transducer over a distance from an original position to a new position relative to the first foot wherein the position of the marker and the new position of the first ultrasound transducer are related by a proportionality constant.

BRIEF DESCRIPTION OF THE DRAWINGS

FIG. 2 contains engineering drawings of a set of parts that together with the parts in FIG. 3 can be used to construct one embodiment of the invention.

FIG. 3 contains engineering drawings of another set of parts that together with the parts in FIG. 2 can be used to construct one embodiment of the invention.

FIG. 5 is a diagram showing another embodiment of an apparatus of the invention that is used to locate a region of interest of a calcaneus in a living being.

DETAILED DESCRIPTION OF THE PREFERRED EMBODIMENT

Figure 1:
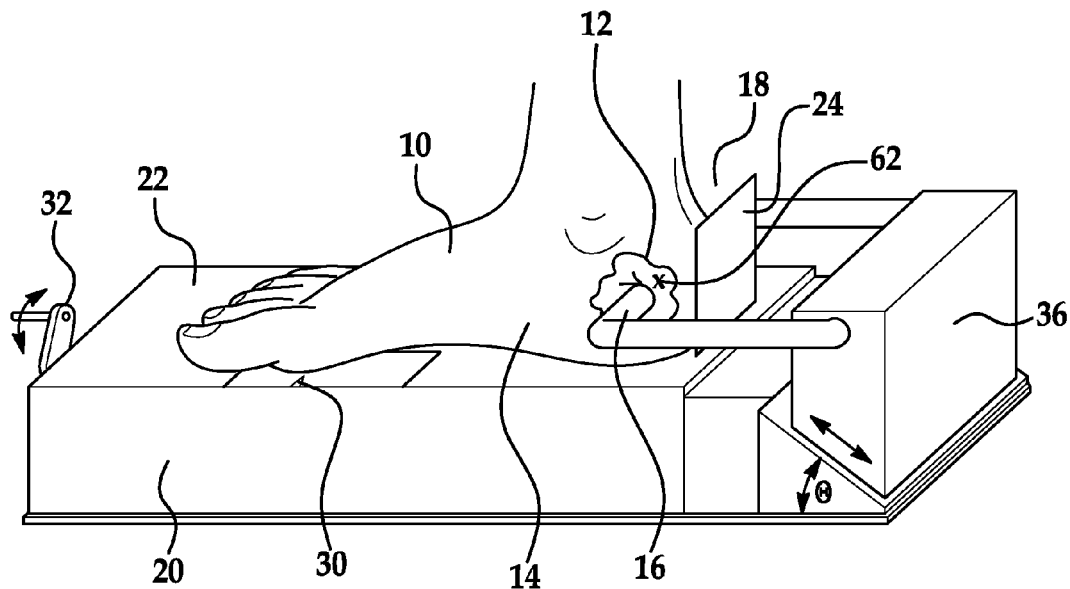
FIG. 1 is a diagram showing the main components of an apparatus of the invention that is used to locate a region of interest of a calcaneus in a living being.

The invention is shown in FIG. 1 is used to locate a region of interest of a calcaneus in a living being for practicing a method of the invention. Specifically, it is intended for locating a region of interest in a calcaneus of a living being that would allow for non-invasively and quantitatively evaluating the status of bone tissue in vivo, as manifested through one or more of the quantities: bone-mineral density, architecture, quality, strength, and fracture risk at a given time. The components of the apparatus are, in general, commercially available from different sources and will be identified before or in the course of the detailed description of their total operation.

Referring to FIG. 1, a calcaneal bone (not shown) within a subject's heel 12 of a foot 10 to be analyzed in vivo is surrounded by a soft tissue having an outer skin surface (skin integument) 14. The heel 12 is to be interposed between two aligned and opposed acoustically coupled ultrasonic transducers 16 and 18 (not viewable behind foot 10) which may be identically the same, and can be obtained from Valpey-Fisher Corp., located in Hopkinton, Mass., United States. As shown, transducer 16 is used for signal launching and the transducer 18 is the receiver for the launched signals after passing through the heel 12, its overlying skin 14, surrounding soft tissue, and also passes through the calcaneus itself (not shown).

As may be seen with further reference to FIG. 1, a subject's foot 10 is placed on a fixture 20, wherein said fixture contains a surface 22 upon which bottom of said foot rests, and a surface 24 upon which back of said foot rests. Implicit in the apparatus shown in FIG. 1 is a selection of a proportionality constant and selection of an angle. The selected proportionality constant, $\alpha$, is the ratio of a linear distance a pair of ultrasound transducers are to be moved (with respect to or from a reference point) at the selected angle divided by a length associated with said subject's foot. In the presently preferred embodiment of the invention, the length associated with said subject's foot is the distance from the back of the heel to the head of the first metatarsal of the foot. With reference to FIG. 1, the location of the head of the first metatarsal is indicated by the marker 30. In the illustrated embodiment, marker 30 is triangular in shape and may be moved longitudinally on, along or proximate to surface 22 of fixture 20 to locate marker 30 at a position relative to foot 10 corresponding to a length or size associated with foot 10. In one constructed embodiment, surface 22 is transparent and marker 30 is disposed below surface 22 so that marker 30 does not contact foot 10. Referring to FIG. 5, in another embodiment of the invention, a marker 70 comprises one or more light emitters, such as light emitting diodes (LEDs) 72, extending longitudinally on, along or proximate to surface 22 of fixture 20. LEDs 72 may again be disposed below surface 22 (which is preferably transparent) so that LEDs 72 do not contact foot 10. The LED 72 located at a position corresponding to the a length or size associated with foot 10 (e.g., at the head of the first metatarsal) may be illuminated. Alternatively, all of the LEDs 72 extending along the length (e.g., from the back of the heel to the head of the first metatarsal) may be illuminated.

Hence, in one embodiment of the invention as shown in FIG. 1, a foot 10 is placed on the surface of a horizontal portion 22 of a fixture 20 which also has a vertical portion 24 against which the back of the foot is placed. Fixture 20 includes a hardware adapted to hold transducers 16, 18 coaxially aligned with one another facing the medial and lateral sides of the subject's heel 12. A threaded rod (underneath the horizontal portion 22 and shown in FIG. 2, 44) is then manually rotated with a crank 32 so that the marker 30 (and also shown in FIG. 2, 46) is brought to be aligned with the head of the first metatarsal of the foot. The threaded rod is also connected, through a series of gears (including in the presently preferred embodiment four pinion and two rack gears as shown in FIG. 2 and FIG. 3), to the transducer fixture so that the transducers are moved along a selected angle $\theta$ a distance proportional to the distance between the back of the foot and the head of the first metatarsal. With additional reference to FIG. 2, threaded rod 44 is rotated and causes a first rack 48 (to which the marker 46 is attached) to move linearly. With additional reference to FIG. 3, the first rack, shown as a dotted line 48 causes a set of four (4) pinion gears to rotate. One gear 50 is directly attached to the first rack. A second gear 51 serves to transfer the rotation in the proper direction to a third gear 52 which is mounted on a shaft to which a fourth gear 53. The fourth gear 53 is in contact with a second rack 60 that moves a piece to which the transducers are attached (see for example component 36 in FIG. 1). In the presently preferred embodiment of the invention, the desired proportionality constant, $\alpha$, is achieved through appropriate selection of the ratio of the number of teeth in pinion gear four 53 to the number of teeth in pinion gear three 52; this is set as the ratio of 15/66 to achieve the desired motion and to locate the desired region of interest.

Figure 6:
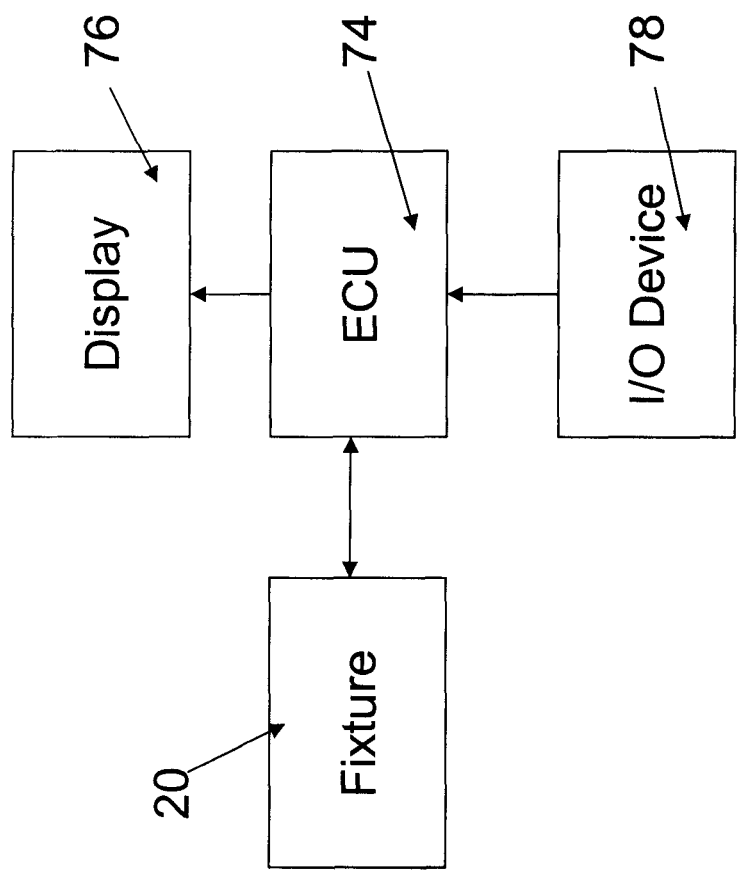
FIG. 6 is a block diagram illustrating another embodiment of an apparatus of the invention that is used to locate a region of interest of a calcaneus in a living being.

Referring again to FIG. 5, in another embodiment of the invention, marker 70 is located and aligned with the first metatarsal of the foot. As described above, crank 32 may be manually rotated to cause rotation of a threaded rod 44 and movement of corresponding racks 48, 60 and gears 50, 51, 52, 53 to move the transducers 16, 18 along a selected angle $\theta$ a distance proportional to a size associated with foot 10 or the contralateral foot of the subject such as the distance between the back of the foot and the head of the first metatarsal. Marker 70 may be electromechanically coupled to this system (e.g., using conventional rotary position encoders and motors) such that the position one or more illuminated LEDs 72 corresponds to, and is indeed related by proportionality constant $\alpha$, to the position of transducers 16, 18. It should be understood that the location of marker 30, 70 and movement of transducers 16, 18 may be accomplished using a variety of mechanical, electronic and fluid (e.g., hydraulic or pneumatic) actuators. Referring to FIG. 6, in another embodiment of the invention, movement of transducers 16, 18 and the location of marker 30 or 70 may be controlled using a conventional electronic control unit (ECU) 74. ECU 74 may form a part of fixture 20. Alternatively, ECU 74 may form part of a separate computing system communicating with appropriate signal processing circuitry in fixture 20 over conventional conductors (i.e., wires or cables)—locally or remotely over a telecommunications network—or wirelessly. ECU 74 may similarly communicate with a display 76 on which, for example, diagnostic measurements may be displayed and an input/output (I/O) device 78 such as a conventional mouse, keyboard or similar device through which, for example, the size associated with foot 10 or the contralateral foot may be input to ECU 74 (e.g. after appropriate measurement using a ruler or a length scale on fixture 20). It should also be understood that I/O device 78 may include a graphical user interface (not shown) on display 76. In view of the proportional relationship between the position of transducers 16, 18 and markers 30, 70, locating markers 30, 70 may cause movement of transducers 16, 18 or movement of transducers 16, 18 may result in the location of marker 30, 70. Referring to FIG. 5, for example, LED(s) 72 of marker 70 may be illuminated through a user input and appropriate control (e.g. through I/O device 78 and ECU 74) to correspond to a size associated with foot 10 or the contralateral foot. Based on which LEDs 72 are illuminated (and therefore the indicated size), ECU 74 may cause a corresponding proportional movement in transducers 16, 18. Alternatively, transducers 16, 18 may be moved through appropriate control by ECU 74 acting on commands received from I/O device 78 and the position of transducers 16, 18 may cause one or more LEDs 72 corresponding to the position to be illuminated. Movement of transducers 16, 18 may continue until the LED or LEDs 72 are illuminated at a position corresponding to the identified size of foot 10 or a contralateral foot (e.g., until the LED 72 positioned at or near the first metatarsal becomes illuminated).

Figure 4:
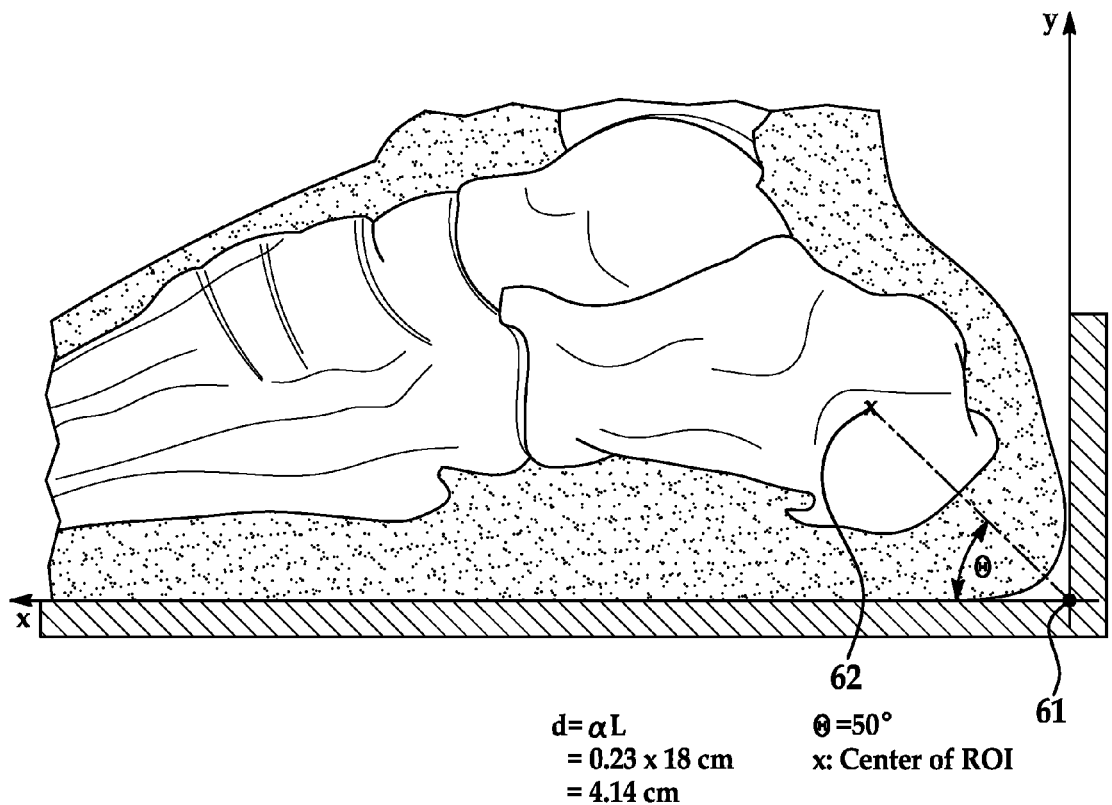
FIG. 4 shows an image of a plain radiograph of a portion of a foot including a calcaneus and the frame of reference used to compute the center of the region of interest.

Therefore, in the presently preferred embodiment, and with additional reference to FIG. 4, the selected angle θ is equal to 50 degrees, and the proportionality constant, α, that is the amount of linear travel of the transducers from the reference point along the given angle of 50 degrees, is 15/66, or approximately 0.23. Therefore, for a ball length of 18 cm, the transducers would be moved a total linear motion (i.e., along a direction of 50 degrees with respect to the horizontal) of 0.23*18 cm=4.14 cm, from a reference point. The reference point 61 for the transducers, in the presently preferred embodiment, is the corner closest to the foot at which the horizontal and vertical portions of the fixture meet. However, it should be appreciated that any point convenient as a reference point may be utilized and is within the scope of the present invention. It is important to appreciate that this procedure will position the transducers at a location overlying the calcaneus that is (1) reproducible and (2) at a position that allows comparisons of bone properties for different subjects to be made with each another. These two factors are key to making the invention disclosed herein useful for non-invasive ultrasound bone assessment, and whereby to achieve the indicated objectives. As may be seen in FIG. 4, the reference point in the presently preferred embodiment is the point at which the vertical and horizontal portions of the fixture meet, indicated by the large dot. The 'x', 62, denotes the center of the identified ROI, over which the center of the transducer or transducers would be placed. The distance d of the center of the ROI to the reference point is equal to αL, where α is the constant of proportionality and L is the size of the relevant portion of the body; in this presently preferred embodiment, α is 0.23 and L=18 cm, the distance from the back of the foot to the head of the first metatarsal. Note that the reference point 61 in this embodiment as shown by the "dot" in FIG. 4 may be understood to correspond to the origin of a frame of reference consisting of an x-axis along the bottom of the foot and a y-axis along the back of the foot, as shown. Note that the parts used to produce the presently preferred embodiment of the invention can be purchased commercially (e.g., from Small Parts, Inc. Small Parts, Inc. of Miami Lakes, Fla., USA) or fabricated by a machining company (e.g., Queen Screw and Manufacturing, Inc., of Waltham, Mass., USA).

Note that in this preferred embodiment of the invention the distance from the back of a foot to the head of the first metatarsal was used as a measure of foot length. It should be understood, however, that the present invention encompasses use of a number of measures of overall foot length, for example the distance between the back of the foot to the end of any of the toes, or some average of a set of such lengths. For example, a measure of foot length from the back of the foot to any point along the ball line (a line that extends from the head of the first metatarsal to the head of the fifth metatarsal) could also be utilized. Therefore, it should be understood that any measure of foot size should be considered to be within the scope of the present invention. This should also be understood to include a length associated with any part of the foot and ankle anatomy, including, for example, a length from the bottom of the heel to the ankle. Of course it is appreciated that with different lengths so defined that different proportions and relationships with transducer motion in general will be necessary. The presently preferred use of the back of the foot and the head of the first metatarsal is due to the ability to locate them both fairly easily as well as the potential artifactual nature associated with the use of the ends of the toes. It should also be understood that the measurement of the size or length of the foot could be taken with respect to the foot that is being ultrasonically measured or the foot that is not being ultrasonically measured (i.e., the contralateral foot) because the sizes associated with the feet of a subject are generally related and close in size.

In addition, it should be understood that different angles (from the presently preferred selection of θ=50°) may also be utilized in the present invention. It should be understood that different angle selections will generally lead to different regions of interest of the calcaneus over which the ultrasound transducers will be located. These distinct regions of interest may prove useful in different aspects of bone assessment, for example as in osteoporosis. For example, one region of interest may prove most useful for assessing changes in bone density while another region of interest may prove most useful for monitoring therapeutic effects on fracture risk. It should also be understood that the values of the specified angle as well as the proportionality constant may be varied to achieve similar but different results (for example to monitor another portion of the calcaneus, or to take into account additional information as to optimal transducer placement), and as such should be considered to be within the scope of the present invention as well.

The invention as embodied in FIGS. 1-3 utilizes manual rotary motion of a threaded rod, together with a set of gears (including rack and pinion) to achieve the desired motion and ultimate location of the transducers. It should be understood, however, that any mechanical device, with gears or without and which may be powered for electronically controlled motion (see, e.g., FIG. 6) or manual or spring powered motion, should also be considered to be within the scope of the present invention. It should also be understood, that although the present embodiment utilizes a fixed ratio of x and y motion (and thus the fixed angle), the present invention should also be understood to include use of nonlinear relationships between the x and y coordinates of the transducer location as a function of length. This may be advantageous when additional information is gained on locating the region of interest, as it may, for example, be necessary for very large or very small feet, or perhaps in distinguishing anatomical variations between men and women.

In yet a further embodiment of the invention, a length not necessarily associated with the foot may be used for purposes of locating a region of interest on the calcaneus. For example, the height of a person may be utilized. Moreover, in this alternative embodiment a set of lengths associated with a variety of (but at least one) bony members of the body is utilized in determining a region of interest of the calcaneus. In general, the set of lengths may be used to independently determine the x and y coordinates of the center of the region of interest. This may be expressed by the following set of equations or relationships:

$$x=f(L1,L2,L3,\ldots,LN)$$

$$y=g(L1,L2,L3,\ldots,LN)$$

where x and y are the location of the region of interest (again with respect to a reference point), and $L1, L2, L3, \ldots, LN$ are the sizes associated with N portions of the body, and where f and g may be suitable functions. Let L1=height, and L2=ball length of the foot; then in a presently preferred embodiment of the invention $$x = a*L1$$

$$y = b*L2$$

As may be seen in this embodiment, the x and y coordinates may not necessarily utilize the same dimensions from a given portion of a body. It should be understood that the invention includes many possible combinations and lengths (sizes) by which to locate the region of interest as specified by x and y. It should further be appreciated that in general f and g may be linear or non-linear functions, and that one may be linear and the other non-linear and visa versa. Note also that a frame of reference must be chosen for identifying the values of x and y.

It should also be appreciated that the center of the location of the region of interest is specified in terms of a set of (x,y) coordinates with respect to a reference frame, and generally is a distance, d, from the origin of the reference frame. It should be understood however that the actual translation or motion of the transducers will not in general be moved a distance d since the starting point of the transducer motion is generally not at the origin.

It should be further appreciated that in an alternative embodiment of the invention, the fixture does not have a vertical portion, but rather a reference mark on the horizontal portion, i.e., a surface of the fixture on which the bottom of the foot rests. It should also be understood that the horizontal surface may not be actually horizontal since it may be convenient to orient it at an angle so that the subject may be comfortable, for example at a 30 degree angle. Similarly, the "vertical portion" of a fixture upon which the back of the foot (heel) rests may not be vertical if the fixture itself is oriented at an angle. Additionally the horizontal surface upon which the bottom of the foot rests may also not be flat, since in some embodiments it may be advantageous to raise or lower the heel with respect to the toes.

It should be appreciated that it an actual measurement of the length of the selected body portion is not always necessary. In the presently preferred embodiment, and with additional reference to FIG. 1, indicator 30 is adjusted through use of crank 32 until it is positioned at the head of the first metatarsal of a foot; this brings, at the same time, the transducers 16, 18, to the desired location on the heel and to the desired region of interest of the calcaneus. In other embodiments, explicit use of the length of a body portion (e.g., overall height of a subject) would need to be measured and utilized. Both kinds of embodiments (i.e., with and without an explicit measurement of length or size of a selected body portion) should be considered to be within the scope of the present invention. Moreover, an embodiment which uses both kinds (i.e., with an explicit and without an explicit measurement of size) should also be considered to be within the scope of the present invention.

It should also be understood that the invention can be utilized with two distinct transducer configurations. The first is with two transducers placed on opposite sides of a subject's heel in a "thru-transmission" mode. In the second, only one transducer may be used, in a "pulse-echo" configuration. In both cases, the methods and apparatuses of the present invention should be understood to be able to locate a desired region of interest of the calcaneus. It also should be appreciated that both pulse-echo and thru-transmission modes can be utilized together with the methods and apparatuses of the present invention.

It should be further appreciated that the disclosed techniques can work with any number of ultrasound signal processing methods and parameters. Therefore, it should be appreciated that any set of ultrasound parameters may be utilized in conjunction with the methods and apparatuses of the present invention. In particular, the methods and apparatuses as disclosed in U.S. Pat. Nos. 5,259,384, 5,651,363, 5,785,656 and 5,879,301, as well as in U.S. patent application No. 20050197576, all of which are incorporated by reference hereinto, and should be understood to be applicable to the present invention.

It should be understood that the methods and apparatuses disclosed herein for locating a region of interest of a calcaneus within a foot of a subject can be utilized not only with ultrasound but with other applications as well, such as for x-ray bone densitometry. In this application, it may be useful for example to measure the thickness of the heel at the region of interest identified by the methods disclosed herein. In this alternative embodiment of the invention, then, ultrasound transducers are not utilized.

It should be further understood that a measurement of overall heel width at the identified region of interest may be of use in various applications, including but not limited to ultrasound bone assessment and x-ray bone assessment. Therefore, it should be understood that in an alternative embodiment of the invention not only is the location of the region of interest identified but a heel width measurement at that location is performed.

It should also be noted that the (x, y) coordinates disclosed hereinabove generally correspond to a center of a region of interest. The region of interest may be of various shapes, such as circular or square. However, it should be understood that a variety of choices for region of interest shape can be made (e.g., triangular or trapezoidal), and that the (x,y) coordinates may be chosen to be not only at the "center" but at other relative locations, and that all of these embodiments should be considered to be within the scope of the present invention. In the presently preferred embodiment of the invention, the region of interest is circular and the (x,y) coordinates are at the geometric center of the circular region of interest.

The invention as described herein achieves the primary objectives of the inventors, namely to locate a region of interest that is clinically relevant to assessment of osteoporosis, adjusts to the size of the calcaneus thereby maintaining the same relative region of interest across subjects, and at the same time maintains excellent reproducibility. While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

What is claimed is:

1. A method for positioning one or more ultrasound transducers at a region of interest in a calcaneus in a first foot of a subject, comprising the steps of:
    placing said first foot in a fixture such that a first ultrasound transducer is disposed on one of a medial side and a lateral side of a heel of said first foot;
    identifying a size associated with one of said first foot and a second foot of said subject;

positioning a marker at a marker position, said marker position corresponding to said size; and, moving said first ultrasound transducer over a distance from an original position to a new position, said new position different from said original position and corresponding to said region of interest wherein said marker position and said new position of said first ultrasound transducer are related by a proportionality constant.

2. The method of claim 1, further comprising the step of moving a second ultrasound transducer disposed on another of said medial side and said lateral side of said heel of said first foot over said distance from an original position to a new position wherein said marker position and said new position of said second ultrasound transducer are related by said proportionality constant.

3. The method of claim 1 wherein said placing step includes a substep of positioning a bottom of said first foot on a first surface of said fixture and a back of said first foot on a second surface of said fixture, said first and second surfaces defining a reference frame.

4. The method of claim 3 wherein said reference frame has an origin at an intersection of said first and second surfaces and said new position of said first ultrasound transducer is at an angle relative to said first surface of said reference frame.

5. The method of claim 4 wherein said new position of said first ultrasound transducer is at an angle relative to said second surface of said reference frame.

6. The method of claim 1 wherein said size is a length from a back of said one of said first foot and a second foot to a head of a first metatarsal of said one of said first foot and a second foot.

7. The method of claim 1 wherein said positioning step and said moving step occur simultaneously.

8. The method of claim 1 wherein said positioning step causes said moving step.

9. The method of claim 1 wherein said moving step causes said positioning step.

10. The method of claim 1 wherein said marker comprises a first light emitting diode.

11. The method of claim 10 wherein said marker comprises a second light emitting diode.

12. An apparatus for positioning one or more ultrasound transducers at a region of interest in a calcaneus in a first foot of a subject, comprising the steps of:

a fixture configured to receive said first foot and including a first ultrasound transducer configured to be disposed on one of a medial side and a lateral side of a heel of said first foot; and a marker indicative of a marker position associated with said first foot, said marker position corresponding to a size associated with one of said first foot and a second foot of said subject; and, means for moving said first ultrasound transducer over a distance from an original position to a new position, said new position different from said original position and corresponding to said region of interest;

wherein said marker position and said new position of said first ultrasound transducer are related by a proportionality constant.

13. The apparatus of claim 12 wherein said moving means includes an electronic control unit configured to receive said size as an input and to generate a control signal as an output, said control signal effecting movement of said first ultrasound transducer.

14. The apparatus of claim 12 wherein said fixture includes a second ultrasound transducer disposed on another of said medial side and said lateral side of said heel of said first foot and said moving means moves said second ultrasound transducer over said distance from an original position to a new position wherein said marker position and said new position of said second ultrasound transducer are related by said proportionality constant.

15. The apparatus of claim 12 wherein said fixture includes a first surface configured to receive a bottom of said first foot and a second surface configured to receive a back of said first foot, said first and second surfaces defining a reference frame.

16. The apparatus of claim 15 wherein said reference frame has an origin at an intersection of said first and second surfaces and said new position of said first ultrasound transducer is at an angle relative to said first surface of said reference frame.

17. The apparatus of claim 16 wherein said new position of said first ultrasound transducer is at an angle relative to said second surface of said reference frame.

18. The apparatus of claim 12 wherein said size is a length from a back of said one foot to a head of a first metatarsal of said one foot.

19. The apparatus of claim 12 wherein said moving means causes movement of said first ultrasound transducer responsive to said marker position.

20. The apparatus of claim 12 wherein said marker assumes said marker position responsive to movement of said first transducer between said original position and said new position.

21. The apparatus of claim 12 wherein said marker comprises a first light emitting diode.

22. The apparatus of claim 21 wherein said marker comprises a second light emitting diode.

* * * * *